United States Patent [19]

Koskinen et al.

[11] Patent Number: 5,426,228
[45] Date of Patent: Jun. 20, 1995

[54] GENERAL METHOD FOR PREPARATION OF SPHINGOSINE BASES AND THEIR ANALOGUES

[76] Inventors: Ari Koskinen; Päivi Koskinen, both of Lepikkotie 2 A 1, FIN-90460 Oulunsalo, Finland

[21] Appl. No.: 265,776
[22] Filed: Jun. 27, 1994
[51] Int. Cl.$^6$ .............. C07C 209/68; C07C 209/62
[52] U.S. Cl. .............................. 564/360; 564/487; 564/507
[58] Field of Search .................. 564/360, 487, 507

[56] References Cited

U.S. PATENT DOCUMENTS 5,012,000  4/1991  Illig et al. ..................... 564/489

OTHER PUBLICATIONS

Synthetic Studies Toward Amino Alcohols. Diasterocontrolled Reduction of α'-Chiral, α,β-Enones. Tetrahedron Letters, vol. 34, No. 42, pp. 6765–6768, 1993.
Horner-Wittig Reaction of Dimethyl 2, 3-O-isopropylidene-D-glyceroylmethylphosphonate and its Application to the formla Synthesis of D-erythro-C$_{1-}$$_8$-Sphingosine, Yamamoi et al., Chemistry Letters, pp. 335–336, 1989.
A Stereodivergent Synthesis of D-erytho-Sphingosine and D-threo-Sphingosine from L-Serine, Garner et al., J. Org. Chem. 1988, 53, pp. 4395–4398.
Synthesis of D-erythro- and D-threo-Sphingosine Derivatives from L-Serine, Herold, Helv. Chim. Acta 71, pp. 354–362, 1988.
A Stereoselective Synthesis of Sphingosine, A Protein Kinase C Inhibitor, Nimkar et al., Tetrahedron Letters, vol. 29, No. 25, pp. 3037–3040, 1988.
α-Amino Acid Derivatives as Chiral Educts for Asymmetric Products Synthesis of Sphingosine from α'-Amino-α,β-ynones, Boutin et al., J. Org. Chem. 1986, 51, pp. 5320–5327.
τ-Amino-β-keto Phosphonates in Synthesis: Synthesis of the Sphingosine Skeleton, Koskinen et al., Synlett, Nov. 1990, pp. 665–666.

*Primary Examiner*—Richard L. Raymond
*Attorney, Agent, or Firm*—Pollock, Vande Sande & Priddy

[57] ABSTRACT

Described herein is a novel method of preparing selectively diastereomers of sphingosine bases and their analogues of general formula (1a) or (1b)

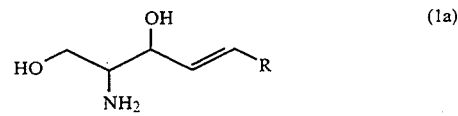

(1a)

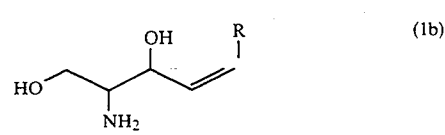

(1b)

where R is an aliphatic or aromatic substituent containing a straight, branched or cyclic chain, which may include one or several heteroatoms as chain members and one or several functional groups as substituents. The method comprises the steps of:

a) converting a starting material into an intermediate product in the form of α,β-unsaturated ketone having the general formula (4a) or (4b)

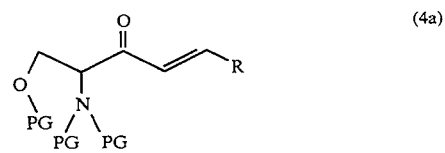

(4a)

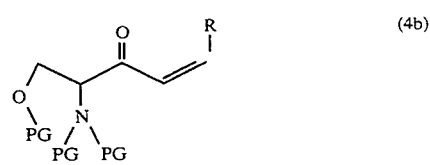

(4b)

where R is as defined above and PG are any protecting groups compatible with the method, b) reducing said α,β-unsaturated ketone to an aminoalcohol with DIBAL in toluene to obtain selectively an anti-diastereomer, and c) removing the protecting groups to obtain the free sphingosine base or its analogue according to formula (1a) or (1b).

1 Claim, No Drawings

GENERAL METHOD FOR PREPARATION OF SPHINGOSINE BASES AND THEIR ANALOGUES

This invention relates to methods of preparing all isomers of sphingosine bases and their analogues which are of general formula (1a) or (1b)

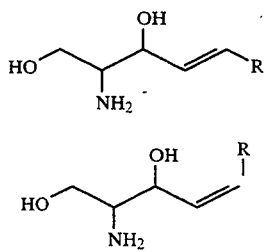

where R is an aliphatic or aromatic substituent containing a straight, branched or cyclic chain, which may include one or several heteroatoms as chain members and one or several functionalities as substituents.

The group of sphingolipids is an important class of membrane constituents that play a major role in cell growth, cell differentiation and cell-cell interactions. Several derivatives of sphingolipids also show tumor-related antigenicity. Sphingosine, an α-aminoalcohol, is the common structural motif in all types of sphingolipids, and also a potent protein kinase C inhibitor. The interest in these compounds has resulted in several published syntheses for sphingosine.

After some racemic syntheses [a) Grob, C. A.; Gadient, F., Helv. Chim. Acta 40, 1145 (1957). b) Shapiro, D.; Segal, H.; Flowers, H. M., J. Am. Chem. Soc. 80, 1194 (1958). c) Schmidt, R. R.; Kläger, R.; Zimmermann, P., Angew. Chem. 3, 215 (1982); Angew. Chem. Int. Ed. Engl. 21, 210 (1982); Fraefel, W.; Schmidt, R. R.; Kläger, R.; Zimmermann, P., Eu Pat. Appl. EP 0 146 810 A2. d) Garigipati, R. S.; Weinreb, S. M., J. Am. Chem. Soc. 105, 4499 (1983). e) Cardillo, G.; Orena, M.; Sandri, S.; Tomasini, C., Tetrahedron 42, 917 (1986).; Bongini, A.; Cardillo, G.; Orena, M.; Sandri, S.; Tomasini, C., J. Chem. Soc. Perkin Trans I, 1345 (1986).; Bongini, A.; Cardillo, G.; Orena, M.; Sandri, S.; Tomasini, C., ibid., 1339 (1986).], a group of syntheses appeared, where the chirality is brought from natural sugar derivatives [a) Reist, E. J.; Christie, P. H., J. Org. Chem. 35, 3521 (1970). b) Koike, K., Nakahara, Y.; Ogawa, T., Glycoconjugate J., 107 (1984).; Koike, K.; Namata, M.; Sugimoto, M.; Nakahara, Y.; Ogawa, T., Carbohydr. Res. 158, 113 (1986). c) Gigg, R.; Conant, R., J. Chem. Soc. Perkin I, 2006 (1977).; Gigg, J.; Gigg, R., Top Curr. Chem. 154, 77 (1990). d) Obayashi, M.; Schlosser, M., Chem. Lett., 1715 (1985). e) Schmidt, R. R.; Zimmermann, P., Tetrahedron Lett. 27,481 (1986).; Schmidt, R. R.; Zimmermann, P., Liebigs. Ann. Chem., 663 (1988). f) Kiso, M.; Nakamura, A.; Tomita, Y.; Hasegawa, A., Carbohydr. Res. 158, 101 (1986). g) Hirata, N.; Yamagiwa, Y.; Kamikawa, T., J. Chem. Soc. Perkin I, 2279 (1991). h) Yadav, J. S.; Vidyanand, D.; Rajagopal, D., Tetrahedron, Lett. 49, 1191 (1993).], or other chiral pool compounds [a) Yamanoi, T.; Akiyama, T.; Ishida, E.; Abe, H.; Amemiya, M.; Inazu, T., Chem. Lett., 335 (1989). b) Somfai, P.; Olsson, R., Tetrahedron Lett. 49, 6645 (1993).]. Sphingosine bases have also been synthesized using enantioselective synthesis methods like asymmetric Sharpless epoxidation [a) Bernet, B.; Vasella, A., Tetrahedron Lett. 24, 5491 (1983).; Julina, R.; Herzig, T.; Bernet, B.; Vasella, A., Helv. Chim. Acta 69, 368 (1986). b) Mori, K.; Umemura, T., Tetrahedron, Lett. 23, 3391 (1982). c) Shibuya, H.; Kawashima, K.; Ikeda, M.; Kitagawa, I., Tetrahedron Lett. 30, 7205 (1989). d) Takano. S.; Iwabuchi, y.; Ogasawara, K., J. Chem. Soc. Communn., 820 (1991).] or enantioselective aldol reaction [a) Nicolau, K. C.; Caulfield, T.; Kataoka, H.; Kumazawa, T., J. Am. Chem. Soc. 110, 7910 (1988). b) Ito, Y.; Sawamura, M.; Hayashi, T., Tetrahedron Lett. 29,239 (1988). c) Groth, U.; Schöllkopf, U.; Tiller, T., Tetrahedron 47, 2835 (1991).] and also using an enzymatic method [Findeis, M. A.; Whitesides, G. M., J. Org. Chem. 52, 2838 (1987).] for introduction of chirality.

The syntheses which have the closest resemblance to our method are based on natural serine as a starting material. The major point of uncertainty and a common feature in all of these is that they use serine aldehyde [a) Newmann, H., J. Am. Chem. Soc. 95, 4098 (1973). b) Tkaczuk, P.; Thornton, E. R., J. Org. Chem. 46, 4393 (1981). c) Funaki, Yo; Kawai, G.; Mori, K., Agric. Biol. Chem. 50, 615 (1986).; Mori, K.; Funakin Y., Tetrahedron 41, 2379 (1985). d) Reetz, M. T., Pure Appl. Chem. 60, 1607 (1988). e) Garner, P.; Park, J. M.; Malecki, E., J. Org. Chem. 53, 4395 (1988). f) Herold, P., Helv. Chim. Acta 71, 354 (1988). g) Nimkar, S.; Menaldino, D.; Merrill, A. H.; Liotta, Tetrahedron Lett. 29, 3037 (1988). h) Radunz, H.-E.; Devant, R. M.; Eiermann, V., Liebigs Ann. Chem., 1103 (1988). h) Dondoni, A.; Fantin, G.; Fogagnolo, M.; Medici, A., J. Chem. Soc., Chem. Comm., 9 (1988).] or its analogues [Boutin, R. H., Rapoport,H., J. Org. Chem. 51, 5320 (1986).] as an intermediate. There is only one known synthesis where serine ester is used [Polt, R.; Peterson, M. A.; DeYoung, L., J. Org. Chem. 57, 5469 (1992).].

Our invention is a method where all four possible isomers of sphingosine can be synthesized independently by using the correct starting material: L- or D-serine and choosing the correct reagent in the later stage. This method has also the advantage of being short, efficient and it does not involve chromatographic purification or separation steps. This method also provides more freedom in choosing the composition of the sidechain than the literature syntheses in general. From now on all the structures are drawn as if L-serine were the starting material of a choice. However, the synthesis proceeds analogously when D-serine is used as a starting material.

SYNTHETIC METHOD

Fully protected serine, methyl (S)-3-(tert-butoxycarbonyl)-2,2-dimethyl-4-oxazolidine carboxylate (2) is converted first to a β-ketophosphonate (3) by a method modified from one used by Koskinen and Krische [Koskinen A. M. P.; Krische, M. J., Synlett, (665 (1990)].

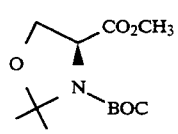

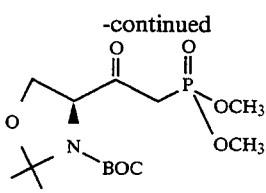

This β-ketophosphonate is converted in a modified Horner-Wadsworth-Emmons manner [a) Koskinen, A. M. P.; Muñoz, L. J. Chem. Soc., Chem. Comm., 652 (1990). b) Koskinen, A. M. P.; Koskinen, P. M., Synlett, 501 (1993).] into an α,β-unsaturated ketone (4).

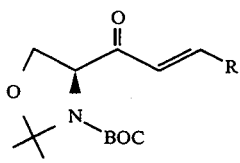

where R is an aliphatic or aromatic substituent containing a straight, branched or cyclic chain, which may include one or several heteroatoms in the chain and one or several functional groups as substituents. In this invention we introduce the method how this ketone (4) can be selectively reduced to either an aminoalcohol of formula (5) with L-selectride$^R$ in THF (syn-diastereomer), or to an aminoalcohol of formula (6) with DIBAL in toluene (anti-diastereomer). The systematic name of L-selectride is lithium tri(sec-butyl)borohydride, Li(sec-Bu)$_3$BH, and that of DIBAL is diisobutylaluminiumhydride, (i-Bu)$_2$AlH.

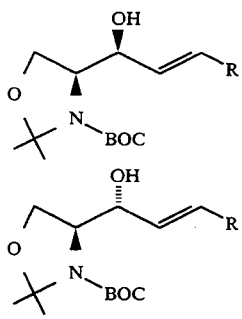

The free sphingosine base corresponding to general formula (1a) can then be easily obtained by removing all the protecting groups in one step [Garner, P.; Park, J. M.; Malecki, E., J. Org. Chem. 53, 4395 (1988).].

The L-selectride in THF has been hypothetically mentioned as a possible reducing agent for the enone intermediate [Koskinen A. M. P.; Krische, M. J., Synlett, 665 (1990).], but it has not been proved experimentally that L-selectride really produces selectively the syn-diastereomer with excellent quantitative results. The use of DIBAL in toluene has not been proposed for producing the anti-diastereomer from the enone intermediate. Since the natural sphingosine is usually present in its anti-diastereomer form, the method of the invention for producing selectively anti-diastereomer sphingosine bases and their derivatives with DIBAL/toluene is of special importance.

From the results it can be further concluded that reducing an enone compound resembling formula (4), but being analogous to a D-serine, with L-selectride in THF will also produce selectively a syn-diastereomer, and reducing this enone compound with DIBAL in toluene will produce selectively an anti-diastereomer.

The invention is not limited to the synthetic route above, but it can be modified within the scope of the claim. All methods having the enone of formula (4) or its D-serine-based analogue as the intermediate product belong to the invention. Further, the invention includes also all syntheses where the initial steps produce an intermediate where the substituent R is in the cis-position and which consequently would result in the product of formula (1b). It is to be understood, that the structure of group R can vary within wide limits, provided that its structure does not affect the qualitative selectivity of the important reducing step. Groups containing an aliphatic chain of at least 5 carbons are preferred, because these groups lead to a total aliphatic skeleton of at least 10 carbons, which contributes to the quantitative selectivity between the syn-and anti-diastereomer. For example a straight carbon skeleton of group R giving a structure close to or identical with sphingosine can be used for attaching a label for radiological research in biology and medicine. The specific isomers obtained by the method of the invention provide thus excellent tools for examining the behavior of sphingosine and its derivatives in biological systems. The isomers of formulae ((1a) and (1b) serve also as intermediates for constructing other useful compounds. As to protecting groups, any groups suitable for protecting the amino and hydroxy functionalities can be applied. For optimum quantitative results in selectively producing an anti- or syndiasteromer, a "cyclic" protecting group bound to both the hydroxy group and amino group and forming a cyclic structure together with said functional groups is preferred.

The invention is described in more detail in the following example, which does not limit its scope.

EXAMPLE

1. Preparation of ((S)-3-(tert-butoxycarbonyl)-4-(2-(dimethoxyphosphoryl)-1-oxo-ethyl)-2,2-dimethyloxazolidine.

Dimethylmethylphosphonate (2.3 ml, 21 mmol, 210 mol-%) was dissolved in 10 ml of THF and cooled to −85° C. (internal temp. −75° C.). To this solution was added 14 ml (1.6M, 21 mmol, 210 mol-%) of n-BuLi in hexanes. The reaction mixture was allowed to warm to −25° C. for 1 hour and then cooled back to −85° C. (internal temp. < −75° C.) after which 2.6 g (10 mmol, 100 ml-%) of methyl ((S)-3-(tert-butoxycarbonyl)-2,2-dimethyl-4-oxazolidine carboxylate was dissolved in 5 ml of THF and cooled to −85° C. (internal temperature < −75° C.). This solution was cannulated onto the anion at such a speed that the internal temperature stayed < −75° C. at all times. After the addition the reaction mixture was allowed to warm to 0° C. very slowly and then it was quenched with 5 w-% citric acid. The pH was adjusted to 3 with sat. citric acid and the reaction mixture was extracted several times with ethyl acetate (EtOAc). Organic phases were washed with brine, combined, dried over Na$_2$SO$_4$ and the solvents were removed in vacuo. The product can be crystallized if necessary from iso-octane. An analytical sample was purified by flash chromatography using 20% EtOAc in hexanes to remove the traces of starting material and then as a stepgradient with 100% EtOAc to remove the excess of dimethylmethylphosphonate to yield 70% of pure 3. Rf, 100% EtOAc: 0.28. mp. 86°–7° C. $^1$H NMR (250 MHz, CDCl3) δ:1.30 (s, 3 H, major rotamer), 1.36 (s, 3 H, minor rotamer), 1.40 (s, 3 H both rotamers), 1.51 (s, 3 H, major rotamer), 1.55 (s, 3 H minor rotamer), 3.06 (d, 2 H, major rotamer, $^2$J(HP)=20 Hz), 3.10 (d, H, minor rotamer, $^2$H(HP)=20 Hz), 3.68 (d, 6 H, $^3$J(HP)=11,2 Hz), 3.91 (dd, 1 H, minor rotamer, J=3.6 Hz, <0.5 Hz), 3.93 (dd, 1 H, major rotamer, J=3.6 Hz, <0.5 Hz), 4.05 (m, 1 H, both rotamers), 4.38 (m, 1 H, major rotamer), 4.48 (m, 1 H, minor rotamer). Rotameric ratio is 2:1 at 20° C. $^{13}$C NMR (50 MHz, CDCl3) δ:23.7 (CH3), 25.0 (CH3), 28.0 (CH3), 52.7 (CH3), 65.0 (c), 65.1 (CH2), 89.8 (c), 94.4 (CH2), 95.(C), 150.9 (C=O), 199.0 (C=O). Anal. Calcd. C 47.86: H 7.46; N 3.99; Found C 48.11; H 7.70; N 4.26. $a^{20}$=−40.1(c=14.0, EtOH).

2. Horner-Wadsworth-Emmons reaction with tetradecanal

The β-ketophosphonate (1.39 g, 3.95 mmol) was dissolved in dry MeCN (25 ml), K2CO3 (1.10 g, 7.90 mmol, 200 mol-%) and teradecanal=C13H27CHO (0.82 g, 3.87 mmol, 98 mol-%) were added at room temperature. The reaction was run at room temperature for 24 h (the reaction was followed with TLC), after which 5 % citric acid (50 ml) was added and the mixture was extracted with 2×50 ml of CH2Cl2. Organic phases were combined, dried and evaporated to dryness to yield 1.55 g of off white solid containing some oily material. This can be used without purification for the next step. For analytical purposes the reaction mixture was purified by flash chromatography using 10% EtOAc in hexanes as an eluent. The purified yield was 1.1 g, 2.51 mmol, 65 % of white waxy solid (Rf, 20% EtOAc/C6:0.37). Chiral HPLC: 80 %ee. $^1$H NMR(200 MHz, CDCl3) γ:0.86 (t, 3 H, J=6.1 Hz), 1.24 (s, 20 H), 1.35 (s, 9 H, major rotamer), 1.47 (s, 9 H, minor rotamer), 1.50(s 3 H, minor rotamer), 1.53 (s, 3 H, major rotamer), 1.63 (s 3 H, minor rotamer), 1.68 (s 3 H, major rotamer), 2,20 (tq, 2 H J=6.1 Hz, 6.9 Hz), 3.88 (dd, 1 H, J=3.7 Hz, 9.2 Hz, major rotamer), 3.93 (dd, 1 H, J=2.8 Hz, 9.3 Hz, minor rotamer), 4.13 (dd, 1 H, J=7.5 Hz, 9.2 Hz, major rotamer), 4.16 (dd, 1 H, J=7.5 Hz, 9.2 Hz) 4.47 (dd 1 H, J=3.7 Hz, 7.5 Hz, major rotamer), 4.67 (dd 1 H, J=2.8 Hz, 7.5 Hz), 6.27 (d, 1 H, J=15.7 Hz, minor rotamer), 6.32 (d, 1 H, J=15.7 Hz, major rotamer), 6.95 (dt, 1 H J=6.9 Hz, 15.7 Hz); rotameric ratio is 2:1. $^{13}$C NMR (50 MHz, CDCl3) 14.1 (CH3), 22.6 (CH2), 24.1 (CH3), 25.2 (CH3), 28.0 (CH2), 28.2 (CH3), 29.2 (CH2), 29.3 (CH2), 29.4 (CH2), 29.6 (CH2), 31.9 (CH2), 32.7 (CH2), 64.0 (CH), 65.9 (CH2), 80.4 (C), 95.1 (C), 125.2 (CH2), 149.6 (CH), 197 (C=O). HRMS (M+$^1$) calcd. 438. 35833, meas. 438.3572. Anal.: Calcd. C 71.35; H 10.82; N 3.20; Found: C 71.03; H 10.92; N 3.08.

4.2 Reduction of the sphingoketone with L-selectride

The sphingoketone of formula (4) (500 mg, 1.14 mmol) was dissolved in 5 ml of THF and the mixture was cooled to −74° C. (internal temperature). L-selectride (3.42 ml, 3.42 mmol, 300 mol-%) was added dropwise. After addition the reaction was allowed slowly to warm to room temperature (ca. 4 h): TLC showed that all starting material had been used and the reaction was then quenched with 5% citric acid (ca. 10 ml, until no gas was evolving) and extracted with 2×20 ml of CH2Cl2. Organic phases were combined, dried and evaporated to dryness to yield compound of formula (5) quantitatively as a pale yellow waxy solid. HPLC showed that it contained >20:1 ratio of syn:anti isomers. An analytical sample was purified by flash chromatography using 10% EtOAc in hexanes as eluento (Rf 20%EtOAc/C6:0.33). $^1$H NMR (200 MHz, CDCl3) δ:0.84 (t, 3 H, J =6.7 Hz), 1.22 (s, 20 H), 1.44 (s, 3 H), 1.46 (s, 9H), 1.53 (s, 3 H), 2.00 (dt, 2 H, J=6.7 Hz, <0.5 Hz), 3.85 (broad m, 2 H, major rotamer), 3.91(broad m, 2 H, minor rotamer), 4.15 (broad m, 1 H major rotamer), 4.32 (broad m, 2 H, minor rotamer), 5.32 (broad m, 2 H, both rotamers), 5.63 (broad t, 1 H, J=6.7 Hz, major rotamer), 5.71 (broad t, 1 H, J=6.7 Hz, minor rotamer). $^{13}$C NMR (50 MHz, CDCl3) δ:14.00 (CH3), 22.6 (CH2), 26.8 (CH3), 27.2 (CH3), 28.3 (CH3), 28.9 (CH2), 29.1 (CH2), 29.2 (CH2), 29.4 (CH2), 29.6 (CH2), 31.8 (CH2), 32.2 (CH2), 61.9 (CH), 64.5 (CH2), 81.2 (C), 94.2 (C), 129.0 (CH), 135.1 (CH). HRMS (M+) calcd. 439.36616, measd. 439.36690.

4.3 Reduction of the sphingoketone with DIBAL

The sphingoketone of formula (4) (500 mg, 1.14 mmol) was dissolved in 10 ml of dry toluene and cooled to −74° C. (internal temperature). DIBAL (3.42 ml (1.0M), 3.42 mmol, 300 m-%) was added dropwise at −74° C. After the addition was complete the reaction mixture was allowed slowly to warm to room temperature (ca. 4 h). TLC showed that all starting material had reacted. Reaction was quenched with 1 N HCl (50 ml) and extracted with 2×50 ml of CH2Cl2. Organic phases were combined, dried and evaporated to dryness yielding 466 mg, 10.5 mmol, 92 % of compound of formula (6) as a pale yellow waxy solid. This material was by HPLC >20:1 of anti:syn diastereomers- An analytical sample was purified by flash chromatography using 10 % EtOAc/hexanes as eluent. (Rf 20% EtOAc/C6:0.23). $^1$H NMR (200 MHz, C6D6, 60° C.), δ:0.96 (t, 3 H, J =6.7 Hz), 1.36 (s, 20 H), 1.42 (s, 12 H), 1.57 (s, 3 H), 2.05 (q, 2 H, J=7.0 Hz), 3.69 (dd, 1 H J=6.3 Hz, 9.8 Hz), 4.04 (broad m, 1 H), 4.32 (broad m, 1 H), 4.50 (dd, 1 H, J=6.9 Hz), 5.57 (dd, 1 H, J=6.9 Hz, 15.3 Hz), 5.75 (ddd, 1 H, J=5.7 Hz, 6.3 Hz, 15.3, Hz). HRMS (M+), calcd. 439.36616, measd. 439.36090. Anal. calcd. C 71.03, H 11.23, N 3.19; measd. C 70.70, H 11.37, N 3.07.

We claim:
1. Method of preparing selectively diastereomers of sphingosine bases and their analogues of general formula (1a) or (1b)

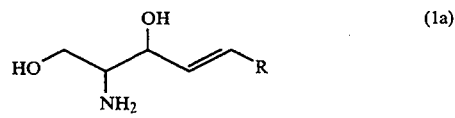

(1a)

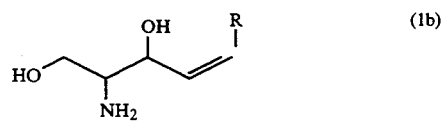

(1b)

where R is an aliphatic or aromatic substituent containing a straight, branched or cyclic chain, which may include one or several heteroatoms as chain members and one or several functional groups as substituents, said method comprising the steps of:
a) obtaining an intermediate product in the form of α,β-unsaturated ketone having the general formula (4a) or (4b)

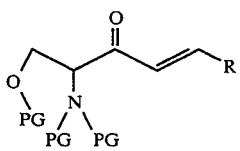
(4a)

-continued

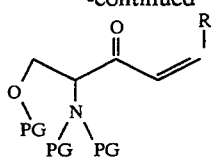
(4b)

where R is as defined above and PG are any protecting groups compatible with the method, said protecting groups including mutually different groups and groups of which two represent a single protecting group common to the amine and hydroxy functionality, b) reducing said α,β-unsaturated ketone to an aminoalcohol with DIBAL ((i-Bu)$_2$AlH) in toluene to obtain selectively an anti-diastereomer, and c) removing the protecting groups to obtain the free sphingosine base or its analogue according to formula (1a) or (1b).

* * * * *